(12) United States Patent
Lee et al.

(10) Patent No.: US 7,419,761 B2
(45) Date of Patent: Sep. 2, 2008

(54) PHOTORESIST MONOMER HAVING SPIRO CYCLIC KETAL GROUP, POLYMER THEREOF AND PHOTORESIST COMPOSITION INCLUDING THE SAME

(75) Inventors: Jae-Woo Lee, Kyungki-do (KR);
Jung-Youl Lee, Kyungki-do (KR);
Deog-Bae Kim, Kyungki-do (KR);
Jae-Hyun Kim, Kyungki-do (KR);
Eun-Kyung Son, Kyungki-do (KR)

(73) Assignee: Dongjin Semichem Co., Ltd. (KR)

( * ) Notice: Subject to any disclaimer, the term of this patent is extended or adjusted under 35 U.S.C. 154(b) by 400 days.

(21) Appl. No.: 11/227,877

(22) Filed: Sep. 15, 2005

(65) Prior Publication Data

US 2006/0057494 A1    Mar. 16, 2006

(30) Foreign Application Priority Data

Sep. 15, 2004  (KR) ................. 10-2004-0073989
Jun. 10, 2005  (KR) ................. 10-2005-0049720

(51) Int. Cl.
*G03F 7/004*  (2006.01)
*G03F 7/30*  (2006.01)
*C08F 34/02*  (2006.01)
*C08F 36/02*  (2006.01)
*C07C 69/74*  (2006.01)

(52) U.S. Cl. ............... 430/270.1; 430/326; 430/910; 526/266; 526/268; 526/270; 526/281; 526/284; 560/116; 560/126; 560/128

(58) Field of Classification Search ............ 430/270.1, 430/326, 905; 526/266, 268, 270, 281; 560/116, 560/126, 128
See application file for complete search history.

(56) References Cited

U.S. PATENT DOCUMENTS

| 4,975,519 | A | | 12/1990 | Yang et al. ................. 528/230 |
| 5,891,603 | A | * | 4/1999 | Kodama et al. ........... 430/270.1 |
| 5,942,367 | A | * | 8/1999 | Watanabe et al. ........... 430/170 |
| 6,027,854 | A | * | 2/2000 | Nishi et al. ............. 430/270.1 |
| 6,136,502 | A | * | 10/2000 | Satoshi et al. ............ 430/270.1 |
| 6,146,811 | A | * | 11/2000 | Kim et al. ............... 430/270.1 |
| 7,288,363 | B2 | * | 10/2007 | Koitabashi et al. ........ 430/270.1 |
| 7,312,016 | B2 | * | 12/2007 | Koitabashi et al. ........ 430/270.1 |
| 2002/0143130 | A1 | | 10/2002 | Lee et al. ................... 526/266 |

FOREIGN PATENT DOCUMENTS

WO    02/20214    3/2002

\* cited by examiner

*Primary Examiner*—John S Chu
(74) *Attorney, Agent, or Firm*—Tuchman & Park LLC

(57) ABSTRACT

A photoresist polymer having a spiro cyclic ketal group, and a photoresist composition including the same is disclosed. The photoresist polymer and the photoresist composition can improve the resolution and the process margin due to its low activation energy of the deprotection reaction of the spiro cyclic ketal group, and can produce fine photoresist patterns due to its low PEB (Post Exposure Baking) temperature sensitivity.

13 Claims, 2 Drawing Sheets

PHOTORESIST MONOMER HAVING SPIRO CYCLIC KETAL GROUP, POLYMER THEREOF AND PHOTORESIST COMPOSITION INCLUDING THE SAME

This application claims priority of Korean Patent Application Nos. 10-2004-0073989 filed on Sep. 15, 2004 and 10-2005-0049720 filed on Jun. 10, 2005.

FIELD OF THE INVENTION

This invention relates to a photoresist monomer having a spiro cyclic ketal group, a polymer thereof and a photoresist composition including the same. More specifically, this invention relates to a photoresist monomer having a spiro cyclic ketal group, a polymer thereof and a photoresist composition including the same, which can improve a resolution, a process margin, and so on, because the activation energy of the deprotection reaction of the spiro cyclic ketal group is low.

BACKGROUND OF THE INVENTION

Recently, as the integration degree and precision of semiconductor devices increase, the formation of ultra-fine photoresist patterns, which have a half pitch of less than 90 nm, is needed in the photolithography process for producing the semiconductor devices. Consequently, the wavelength of an exposure light is reduced to less than 193 nm, and various technologies for optimizing the wafer forming process and making a precise wafer have been being developed. In addition, in order to form the fine photoresist patterns, it is also necessary to develop photosensitive materials having a low LER (Line Edge Roughness), a low PEB (Post Exposure Baking) temperature sensitivity, and a good dry etching resistance.

In order to improve the resolution and the process margin in the process for forming the photoresist pattern, and to produce a more fine photoresist pattern, the photosensitive photoresist polymer should have a low activation energy in the deprotection reaction of the protecting group, in which the protecting group is adhered to the chain of the photoresist polymer for inhibiting the dissolution of the polymer against a basic solution, and/or a low PEB (Post Exposure Baking) temperature sensitivity. For example, the photoresist polymers which can be used for ArF exposure light source include polyacrylate, cycloolefin-maleic anhydride copolymer, polynorbornene and so on, and they are classified into (i) a polymer having the high activation energy protecting group, such as a tertiary butyl group, (ii) a polymer having the medium activation energy protecting group, such as a methyl adamantyl group or an ethyl adamantyl group, and (iii) a polymer having the low activation energy protecting group, such as an acetal group or a ketal group, according to the magnitude of the activation energy of the deprotection reaction of the protecting group which is adhered to the chain of the polymer. As the photoresist polymer for ArF exposure light source, poly(meth)acrylate having acetal groups, which belong to the low activation energy protecting group, is disclosed in U.S. Pat. No. 4,975,519, U.S. Patent Publication No. 2002-0143130(2002.10.03) and International patent publication No. WO 2002-20214(2002.3.14) and so on.

SUMMARY OF THE INVENTION

Therefore, it is an object of the present invention to provide a photoresist monomer having a spiro cyclic ketal group, a polymer thereof and a photoresist composition including the same, which can improve a resolution, and a process margin due to the low activation energy of the deprotection reaction of the spiro cyclic ketal group, and which can produce fine photoresist patterns due to the low PEB (Post Exposure Baking) temperature sensitivity.

It is other object of the present invention to provide a photoresist monomer having a spiro cyclic ketal group, a polymer thereof and a photoresist composition including the same, which can improve the focus depth margin and the line edge roughness of the photoresist patterns.

It is another object of the present invention to provide methods of producing the monomer and the polymer thereof, and a method of forming the photoresist pattern using the above-mentioned photoresist composition.

To accomplish these and other objects, the present invention provides a monomer having a spiro cyclic ketal group, which is represented by the following Formula 1.

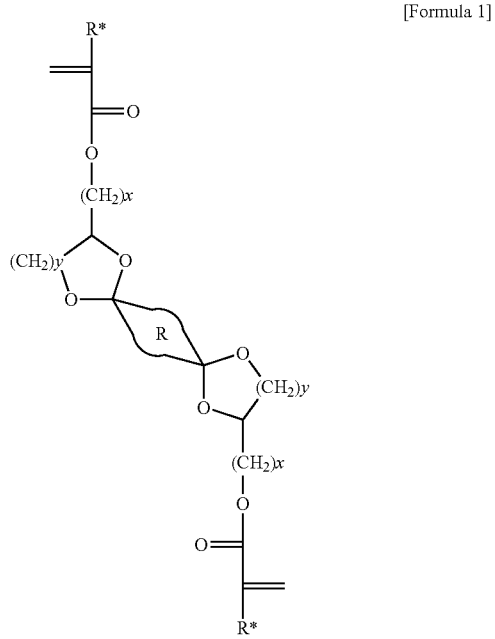

[Formula 1]

In Formula 1, R* is hydrogen or methyl group, x and y are independently 1, 2 or 3, and R is a mono-cyclic or multi-cyclic homo or hetero saturated hydrocarbyl group of 3 to 50 carbon atoms.

The present invention also provides a polymer having a spiro cyclic ketal group, which includes the repeating unit of the following Formula 2.

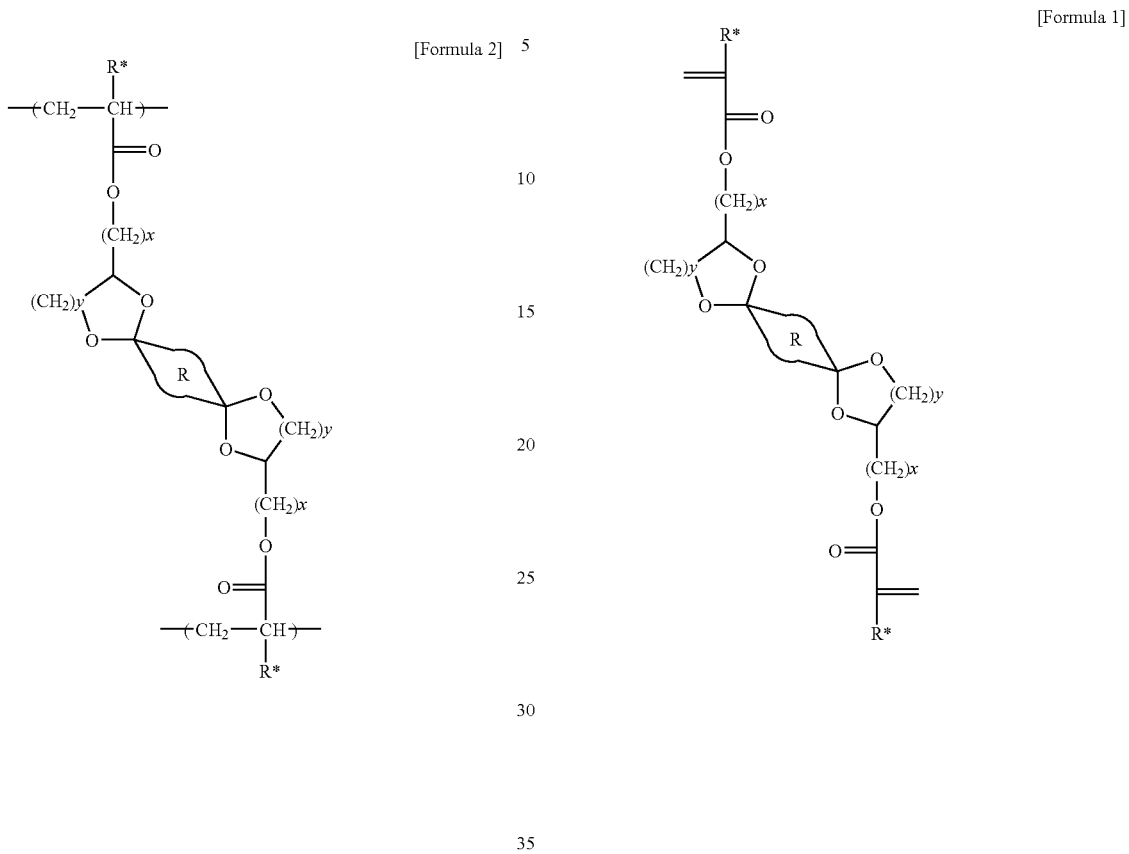

[Formula 2]

[Formula 1]

In Formula 2, R*, R, x and y are as defined in Formula 1.

The present invention also provides a photoresist composition including the above-mentioned polymer and a method of forming the photoresist pattern using the above-mentioned photoresist composition.

In Formula 1, R* is hydrogen or methyl group, x and y are independently 1, 2 or 3, and R is a mono-cyclic or multi-cyclic homo or hetero saturated hydrocarbyl group of 3 to 50 carbon atoms. Preferably, R is

BRIEF DESCRIPTION OF DRAWINGS

A more complete appreciation of the invention, and many of the attendant advantages thereof, will be better understood by reference to the following drawings, wherein.

DETAILED DESCRIPTION OF PREFERRED EMBODIMENTS

Figure 1:
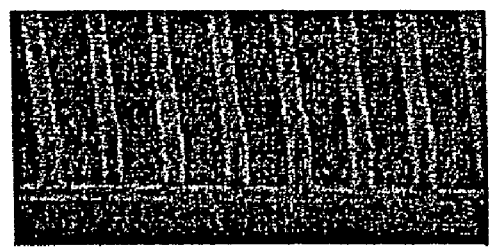
FIGS. 1 to 11 are SEM (Scanning Electron Microscopy) pictures of photoresist patterns which were formed with the photoresist composition according to the examples of the present invention.

Hereinafter, the present invention will be explained in more detail by reference to the appended drawings.

The photoresist monomer having a spiro cyclic ketal group according to the present invention can be represented by the following Formula 1.

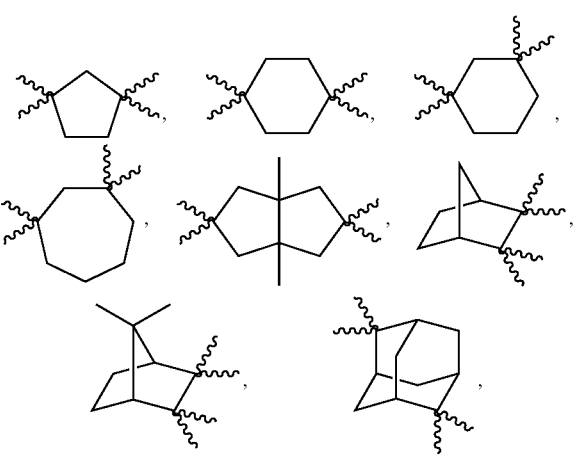

-continued

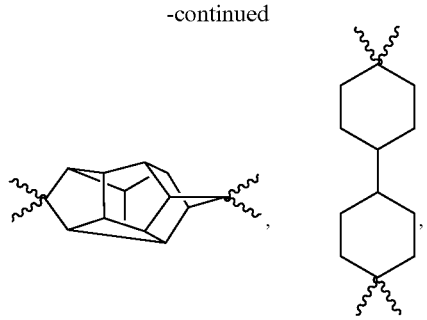

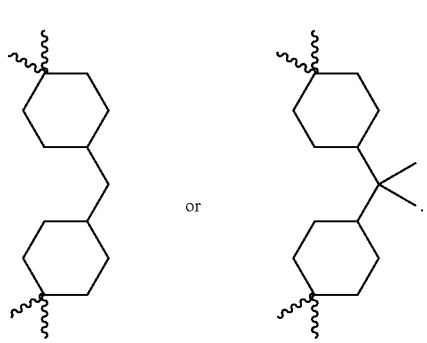

Here, the spiral line (∼∼∼) means a connecting bond).

The monomer having a spiro cyclic ketal group according to the present invention, which is represented by the Formula 1, can be prepared by conventional organic synthetic methods. For example, as shown in the following Reaction 1, a cyclic ketal alcohol is prepared by the reaction of cyclic ketone and trialcohol in the presence of an acid catalyst.

lyst is p-toluene sulfonic acid. The reaction can be carried out under nitrogen or argon atmosphere, at the temperature of 30 to 100° C. and at room pressure, for 1 to 24 hours, in the conventional organic solvent, such as normal heptane. Then, as shown in the following Reaction 2, the monomer represented by Formula 1 can be prepared by reaction of the obtained cyclic ketal alcohol and (meth)acryloyl chloride in the presence of a basic catalyst.

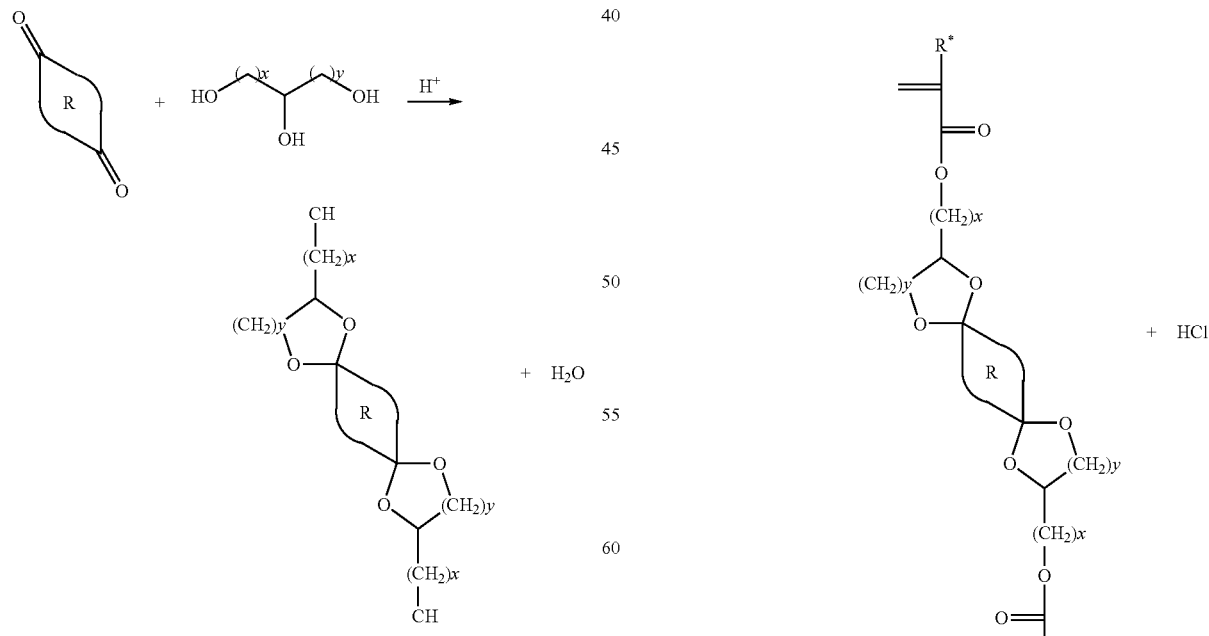

In Reaction 1, R, x and y are as defined in Formula 1.

As the acid catalyst, conventional various acid catalysts can be used, and the representative example of the acid cata- In Reaction 2, R*, R, x and y are as defined in Formula 1.

As the basic catalyst, conventional various basic catalysts can be used, and the representative example of the basic catalyst is triethylamine. The reaction can be carried out under inert atmosphere including nitrogen, argon, and so on, at the temperature of 0 to 60° C. and at room pressure, for 1 to 24 hours, in the conventional organic solvent, such as tetrahydrofuran (THF).

The photoresist polymer having a spiro cyclic ketal group according to the present invention includes the repeating unit of the following Formula 2.

In Formula 2, R*, R, x and y are as defined in Formula 1.

In the photoresist polymer according to the present invention, the repeating unit of Formula 2 can be included in the amount of 1~99 mol % and 1~99 mol % at the upper and the lower polymer chains, respectively. The amounts are on the basis of the total repeating units at the upper or the lower polymer chain. The more preferable amounts of the repeating unit of Formula 2 are 5~95 mol % and 5~95 mol % at the upper and the lower polymer chains, respectively. As monomers which can be used together with the repeating unit of Formula 2, various monomers which are conventional in producing photoresist polymer can be used.

The preferable photoresist polymer having the spiro cyclic ketal group according to the present invention is a polymer which is represented by the following Formula 3, and the more preferable polymers can be represented by Formulas 3a to 3e.

[Formula 2]

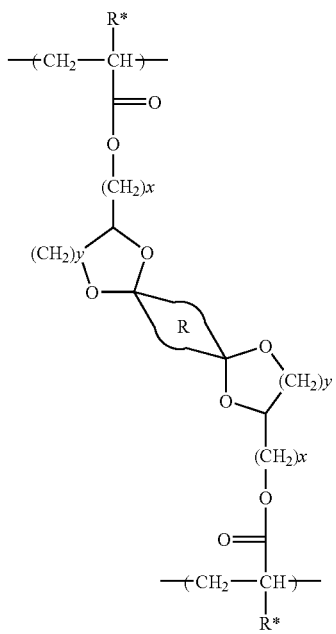

[Formula 3]

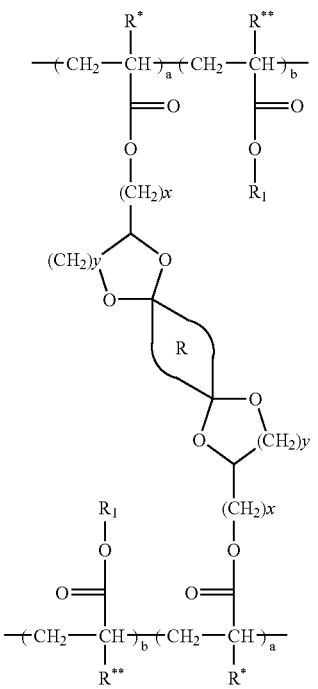

[Formula 3a]
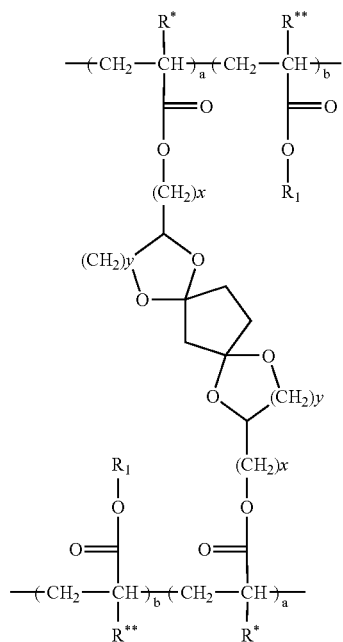
[Formula 3b]
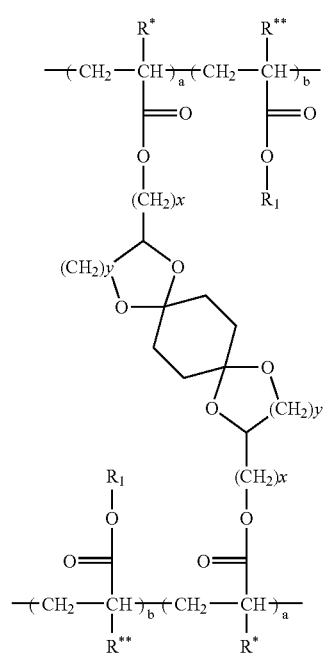
[Formula 3c]
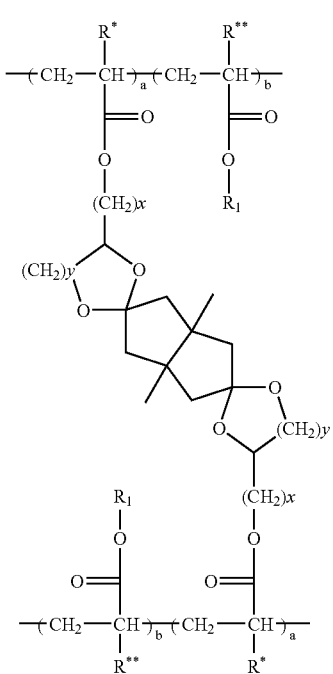
[Formula 3d]
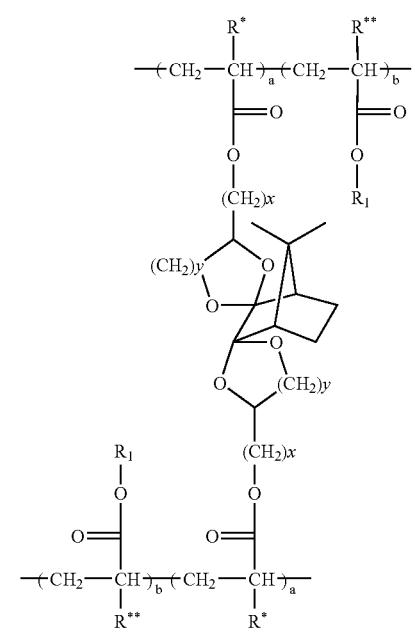

[Formula 3e]

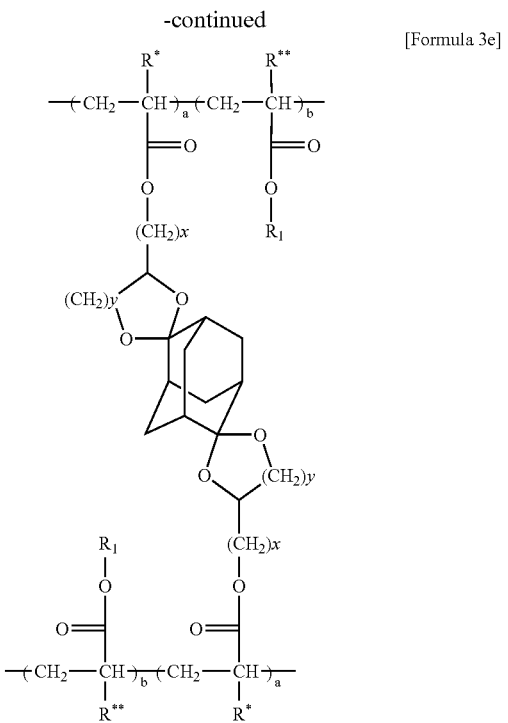

In Formulas 3 and 3a to 3e, R* and R** are independently hydrogen or a methyl group, $R_1$ can be the same or different, and is a chain type or ring type alkyl group of 1 to 20 carbon atoms, a and b are mole % of the repeating units composing the upper and lower polymer chains, and are independently 1~99 mol % and 1~99 mol %, preferably 1~95 mol % and 1~95 mol %, and more preferably 5~95 mol % and 5~95 mol %, and x, y, and R are as defined in Formula 1. The polymer can be a block copolymer or a random copolymer.

Other preferable photoresist polymers having a spiro cyclic ketal group according to the present invention can be represented by the following Formulas 4 and 5, and the more preferable polymers can be represented by Formulas 5a to 5f.

[Formula 4]

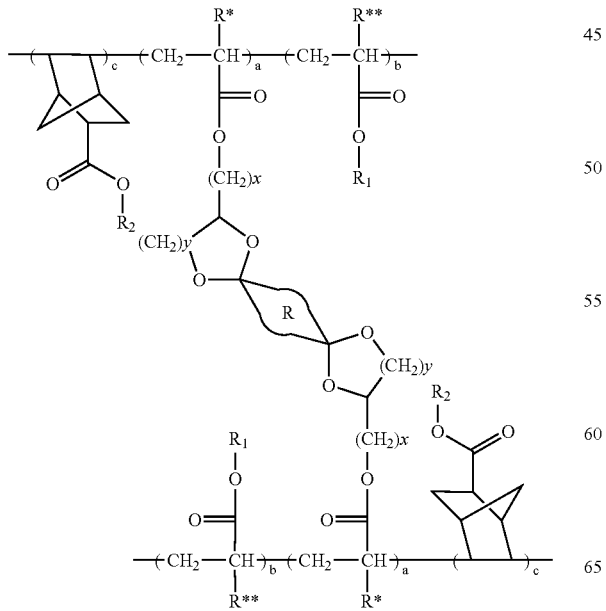

In Formula 4, R* and R** are independently hydrogen or a methyl group, $R_1$ can be the same or different, and is a chain type or ring type alkyl group of 1 to 20 carbon atoms, R is a mono-cyclic or multi-cyclic homo or hetero saturated hydrocarbyl group of 3 to 50 carbon atoms, x and y are independently 1, 2, or 3, and a, b and c are mole % of the repeating units composing the upper and lower polymer chains, and are independently 1~95 mol %, 1~95 mol %, and 1~95 mol %.

[Formula 5]

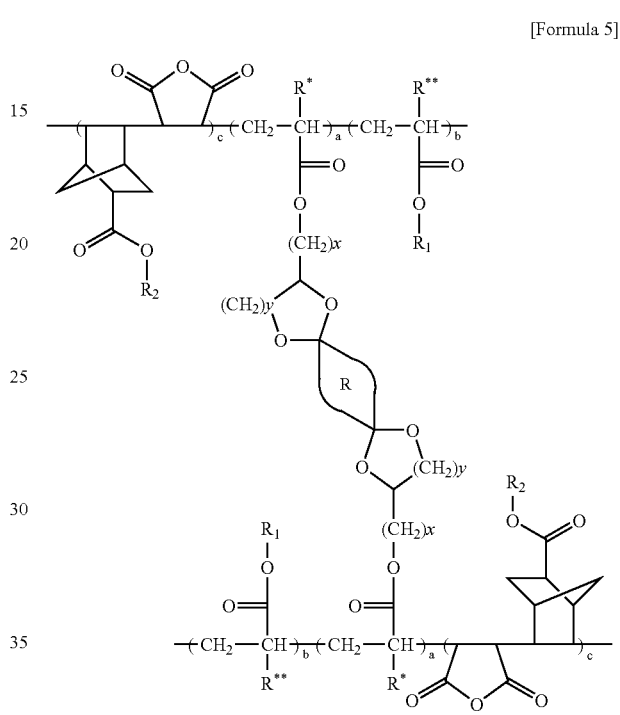

[Formula 5a]

[Formula 5b]
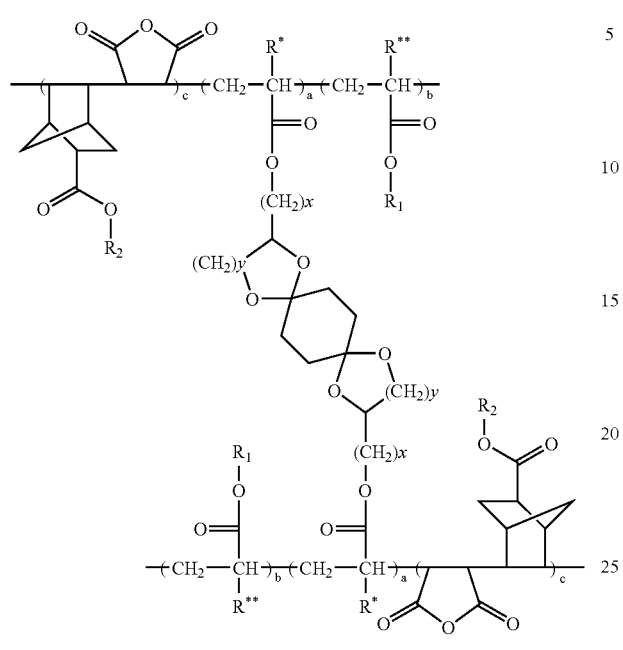
[Formula 5d]
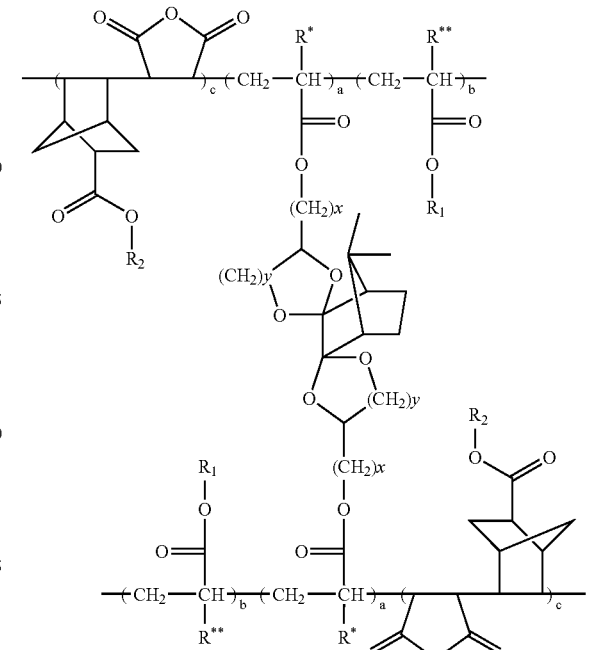
[Formula 5c]
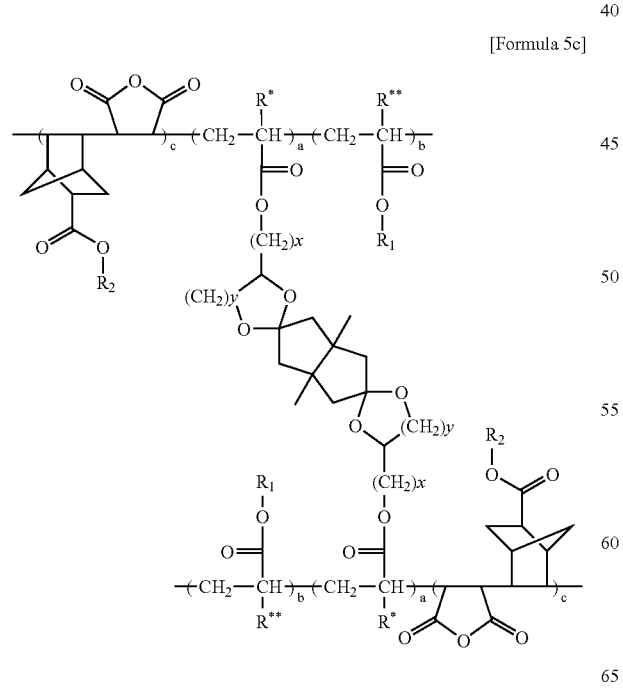
[Formula 5e]
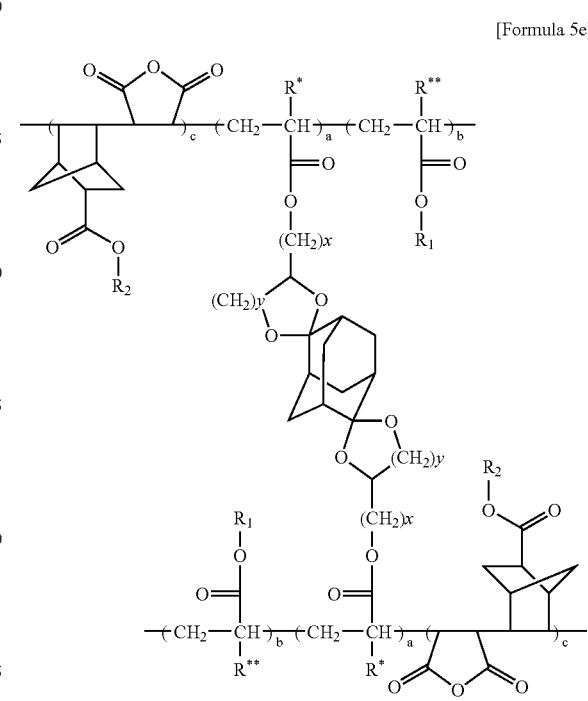

-continued

[Formula 5f]

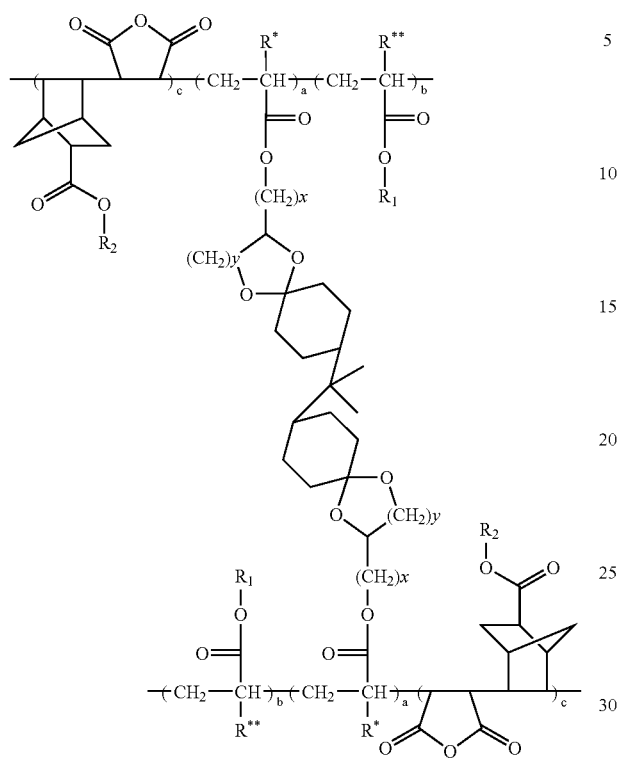

In Formulas 5 and 5a to 5f, $R^*$, $R^{**}$, $R$, $R_1$, $R_2$, a, b, c, x and y are as defined in Formula 4.

The spiro cyclic ketal group, which is a bulky saturated hydrocarbyl group and adhered to the chain of polymer, is a protecting group for preventing the polymer and a photoresist composition including the same from being dissolved by a basic solution, such as a basic developing solution. The protecting group is deprotected by an acid catalyst ($H^+$) which is produced from a photo-acid generators when exposed to an exposure light. Then, the solubility of the exposed region increases, and the contrast of the photoresist composition is effectively improved. Especially, the spiro cyclic ketal group can improve the resolution of the resist pattern, and the process margin, such as an energy margin due to its low activation energy of the deprotection reaction. In addition, the spiro cyclic ketal group can improve the focus depth margin and the line edge roughness because the product of deprotection reaction is a bulky material of high molecular weight. The norbornene monomer, which is used together with the monomer having the spiro cyclic ketal group for composing the polymer, decreases the flexibility of poly(meth)acrylate polymer, and maintains the resist to be rigid.

The photoresist polymer including the repeating unit of Formula 2 can be prepared by the steps of (a) dissolving one more monomers including the monomer of Formula 1 and a polymerization initiator in a polymerization solvent, and (b) reacting the reaction solution under the inert atmosphere of nitrogen, argon, and so on, at the temperature of 60 to 70□ for 4 to 24 hours. The polymerization reaction can be carried out by a radical polymerization reaction, a solution polymerization reaction, a bulk polymerization reaction or a polymerization reaction using a metal catalyst. The polymerization method may further include the step of crystallizing and purifying the reaction product with diethyl ether, petroleum ether, a lower alcohol, such as methanol, ethanol or isopropanol, water, the mixtures thereof, or so on.

As other monomer component, which can be used together with the monomer of Formula 1, conventional various monomers for producing a photoresist polymer can be used. Exemplary conventional monomers include, but are not limited to, (i) a monomer having an acid-sensitive protection group, for example, t-butyl, tetrahydropyran-2-yl, 2-methyl tetrahydropyran-2-yl, tetrahydropyran-2-yl, 2-methyl tetrahydropyran-2-yl, 1-methoxypropyl, 1-methoxy-1-methylethyl, 1-ethoxypropyl, 1-ethoxy-1-methylethyl, 1-methoxyethyl, 1-ethoxyethyl, t-butoxyethyl, 1-isobuthoxyethyl and 2-acetylmenth-1-yl for example, (ii) a monomer of the following Formula 6, and (iii) a cycloolefin monomer such as maleic anhydride. Specific example of the conventional monomers includes 2-methyl-2-adamantyl(meth)acrylate.

[Formula 6]

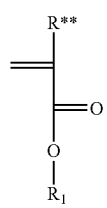

In Formula 6, $R^{**}$ and $R_1$ are as defined in Formula 3.

As shown in the following Reaction 3, the photoresist polymer of Formula 3 can be prepared by reaction of the monomer of Formula 1 and the monomer of Formula 6.

[Reaction 3]

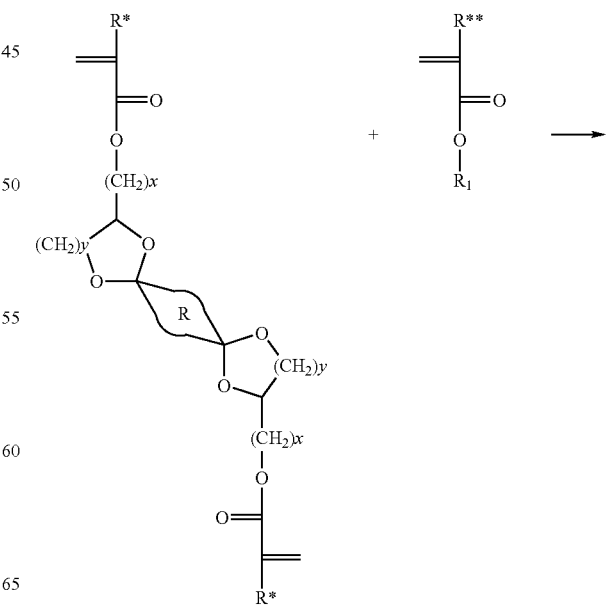

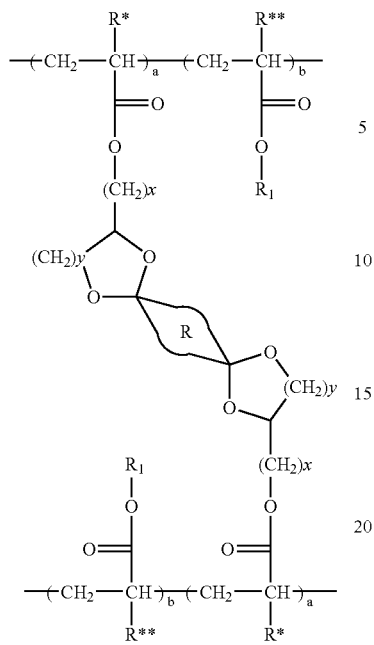
In Reaction 3, R*, R**, R, $R_1$, x, y, a and b are as defined in Formula 3.
Also, as shown in the following Reaction 4, the photoresist polymer of Formula 5 can be prepared by reaction of the monomer having the spiro cyclic ketal group of Formula 1, a monomer having a norbornene group, maleic anhydride and the monomer of Formula 6.
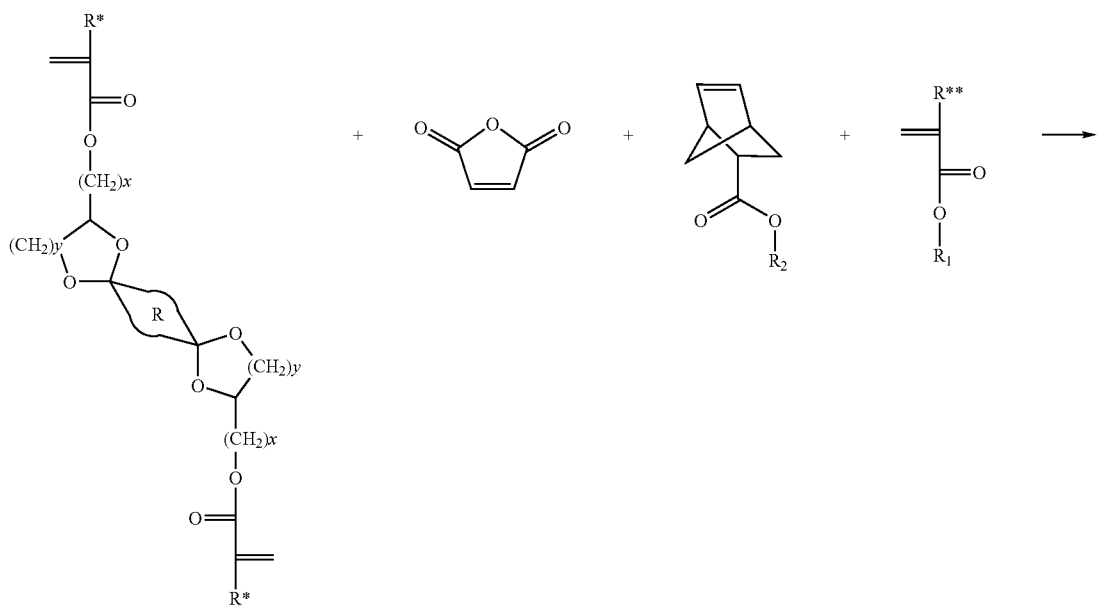
[Reaction 4]

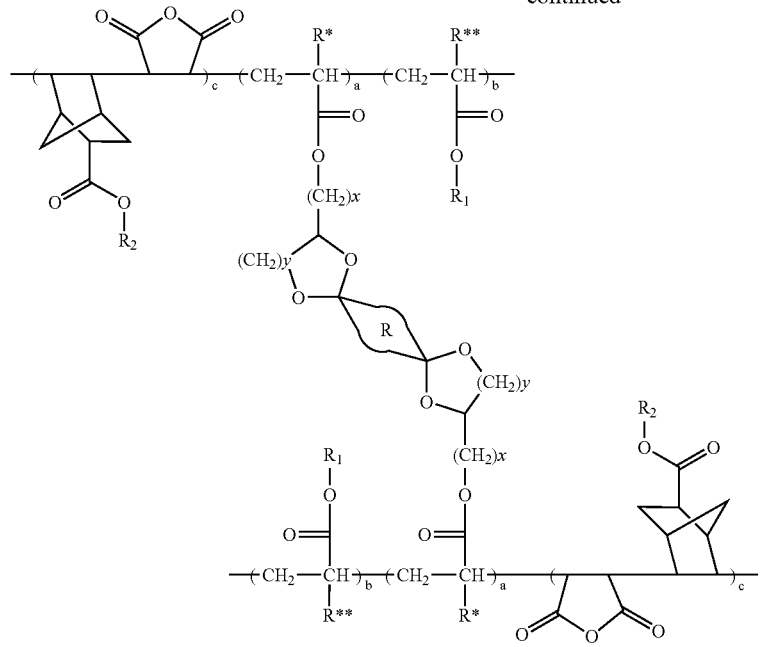

In Reaction 4, R*, R**, R, R$_1$, R$_2$, x, y, a, b and c are as defined in Formula 4.

The monomer having a norbornene group used in Reaction 4 can be prepared by the Diels-Alder reaction shown in the following Reaction 5.

[Reaction 5]

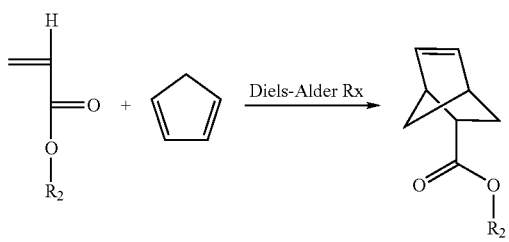

In Reaction 5, R$_2$ is a chain type or ring type alkyl group of 1 to 20 carbon atoms.

As one of the method for preparing the norbornene monomer, the Diels-Alder reaction can be effectively used in the present invention to synthesize the norbornene monomer having a protecting group.

As the polymerization solvent, conventional various polymerization solvents for producing a photoresist polymer can be used. Exemplary polymerization solvents include, but are not limited to, cyclohexanone, cyclopentanone, tetrahydrofuran, dimethylformamide, dimethylsulfoxide, dioxane, methylethylketone, benzene, toluene, xylene, and the mixtures thereof. Polymerization initiator also can be selected from conventional various polymerization initiators. Exemplary polymerization initiators include benzoylperoxide, 2,2'-azobisisobutyronitrile (AIBN), acetylperoxide, lauyl peroxide, t-butylperacetate, t-butylhydroperoxide, di-t-butylperoxide and the mixtures thereof, which are well known to those skilled in the art. The preferable weight average molecular weigh (Mw) of the photosensitive polymers of Formulas 2 to 3 is from 3,000 to 100,000, and the preferable polydispersity (PD) of the polymers is from 1.0 to 5.0. If the weight average molecular weight (Mw) and the polydispersity (PD) of the polymers are out of the range, the property of photoresist layer and the contrast of patterns can be deteriorated or the photoresist layer cannot be formed.

The photoresist composition according to the present invention includes the photosensitive polymer including the repeating unit of Formula 2, a photo-acid generator for producing an acid component, and an organic solvent. If necessary, the photoresist composition may further include various additives. The preferable amount of photosensitive polymer including the repeating unit of Formula 2 is 1 to 30 weight %, and more preferably 5 to 15 weight % for the total amount of the photoresist composition. If the amount of the photosensitive polymer is less than 1 weight %, the formation of patterns having desired thickness is in trouble, because the resist layer becomes too thin. If the amount of the photosensitive polymer is more than 30 weight %, the uniformity of the coating layer may be deteriorated.

The photo-acid generator produces an acid component such as H$^+$ when exposed to a light source. Therefore, the photo-acid generator deprotects the protection group of the photosensitive polymer. As the photo-acid generator, any compound, which can generate an acid component when exposed to light, can be used. Preferable examples of the photo-acid generator include sulfonium compound such as organic sulfonic acid, onium compound such as onium salt, and the mixtures thereof. The non-limiting examples of the photo-acid generator include phthalimidotrifluoromethane sulfonate, which has a low light absorbance at 157 nm and 193 nm, dinitrobenzyltosylate, n-decyl disulfone, naphthylimido trifluoromethane sulfonate, diphenyliodonium hexafluorophosphate, diphenyliodonium hexafluoroarsenate, diphenyliodonium hexafluoroantimonate, diphenylparamethoxyphenylsulfonium triflate, diphenylparatoluenylsulfonium triflate, diphenylpara-isobutyl phenylsulfonium triflate, triphenylsulfonium hexafluoroarsenate, triphenylsulfonium hexafluoro antimonate, triphenylsulfonium triflate, dibutylnaphthylsulfonium triflate and the mixtures thereof.

The preferable amount of the photo-acid generator is from 0.05 to 10 weight % for the amount of the photoresist polymer (namely, from 0.05 to 10 weight parts for 100 weight parts of the polymer). If the amount of the photo-acid generator is less than 0.05 weight %, the deprotection of the protection group be may in trouble, because the sensitivity of the photoresist composition against light decreases. If the amount of the photo-acid generator is more than 10 weight %, the profile of the resist patterns may be deteriorated because a large quantity of acid is produced from the photo-acid generator.

The remaining component of the photoresist composition according to the present invention is the organic solvent. The organic solvent can be selected from conventional various solvents, which are used for the preparation of a photoresist composition. Exemplary organic solvent include, but are not limited to, ethyleneglycol monomethylether, ethyleneglycol monoethylether, ethyleneglycol monoacetate, diethyleneglycol, diethyleneglycol monoethylether, propyleneglycol monomethyletheracetate, propyleneglycol, propyleneglycol monoacetate, toluene, xylene, methylethylketone, methylisoamylketone, cyclohexanone, dioxane, methyl lactate, ethyl lactate, methylpyruvate, ethyl pyruvate, methylmethoxy propionate, ethylmethoxy propionate, N,N-dimethyl formamide, N,N-dimethyl acetamide, N-methyl 2-pyrrolidone, 3-ethoxyethylpropionate, 2-heptanone, gamma-butyrolactone, ethyl 2-hydroxy propionate, ethyl 2-hydroxy-2-methyl propionate, ethoxyethyl acetate, hydroxyethyl acetate, methyl 2-hydroxy-3-methylbutanoate, methyl 3-methoxy-2-methylpropionate, ethyl 3-ethoxy propionate, ethyl 3-methoxy-2-methylpropionate, ethyl acetate, butyl acetate and the mixtures thereof.

If necessary, the photoresist composition may further include organic base. Exemplary organic bases include, but are not limited to, triethylamine, triisobutylamine, triisooctylamine, diethanolamine, triethanolamine and the mixtures thereof. The preferable amount of the organic base is from 0.01 to 2.00 weight % for the total amount of photoresist composition. If the amount of the organic base is less than 0.01 weight %, the undesirable T-Top phenomenon may be occurred at the resist pattern. If the amount of the organic base is more than 2.00 weight %, the pattern forming rate may be lowered because the sensitivity of photoresist composition decreases.

The photoresist composition according to the present invention can be prepared by mixing the photosensitive polymer, the acid generator, the organic solvent, and, if necessary, various additives, and by filtering the mixture. Here, the preferable concentration of the solid components in the composition is from 10 to 60 weight %. If the concentration of the solid components is less than 10 weight %, the formation of patterns having a desirable thickness may be in trouble, because the coated resist layer becomes too thin. If the concentration of the solid components is more than 60 weight %, the uniformity of the coating layer may be deteriorated.

In order to form the photoresist pattern with the photoresist composition according to the present invention, the following conventional photolithography process can be carried out. First, the photoresist composition is applied on a substrate such as silicon wafer, an aluminum substrate, and so on, for example, with a spin coater to form a photoresist layer. Subsequently, the photoresist layer is exposed to a light source to form a predetermined pattern. After the exposure, if necessary, the photoresist pattern is thermally treated, which is referred to as a PEB (Post Exposure Bake) and is developed. The prepared photoresist pattern is used to produce a semiconductor having a predetermined circuit patterns. As the developing solution for the developing process, alkali solution including alkali compounds such as sodium hydroxide, potassium hydroxide, sodium carbonate, tetramethylammonium hydroxide (TMAH) of the concentration of 0.1 to 10 weight % can be used. If necessary, the developing solution may further include water-soluble organic solvent such as methanol, ethanol and surfactant with a proper amount. After carrying out the developing process, the cleaning process of the substrate can be carried out, in which the substrate is washed with purified water.

Hereinafter, the preferable examples of the present invention are provided for better understanding of the present invention. However, the following examples are to illustrate the present invention, and the present invention is not limited to the following examples.

EXAMPLE 1-1

Preparation of Monomer of Formula 7a

After adding 24.0 g (0.26 mol) of glycerol, 9.8 g (0.1 mol) cyclopentane-1,3-dione, 0.15 g of para-toluene sulfonic acid, and 60 g of normal heptane into 500 mL 3 necks round-bottom flask, Dean-Stark trap was installed at the flask. Thereafter, the reaction mixture was refluxed under nitrogen atmosphere at 98□ for 12 hours. After completion of the reaction, the reaction solution was cooled to room temperature. The cooled reaction solution was placed in a separatory funnel, and the separated and unreacted polyols were removed. Thereafter, spiro cyclic ketal alcohol, which was obtained by removing polyols was purified by column chromatography. The purified spiro cyclic ketal alcohol was placed in 3 necks round-bottom flask, and was diluted by adding 30 g of tetrahydrofuran (THF). 20.8 g of methacryloyl chloride (or 18.2 g acryloyl chloride) and 50 g of tetrahydrofuran (THF) were added into the diluted reactant with a dropping funnel. Thereafter, 10 mL of triethylamine was added, and refluxed under nitrogen atmosphere for 12 hours. After completion of the reaction, the solvent was removed by vacuum distillation of the reactant. Thereafter, the reactant was separated by a liquid chromatography (silica gel, hexane:ether=6:1), and the solvent was removed again. The reactant, which did not contain solvent was recrystallized by hexane, and then the recrystallized reactant was stayed at the room temperature to obtain the monomer represented by the following Formula 7a with 55% yield. {H-NMR: i)R*=H, d(6.52, 2H), m(6.16, 2H), d(5.98, 2H), m(4.56, 2H), m(4.31, 4H), m(3.91, 4H), m(3.63, 2H), m(1.96, 6H) ii) R*=CH$_3$, s(6.56, 2H), d(5.86, 2H), m(4.96, 2H), m(4.63, 4H), m(4.42, 4H), m(3.69, 2H), m(1.35, 12H)}

[Formula 7a]

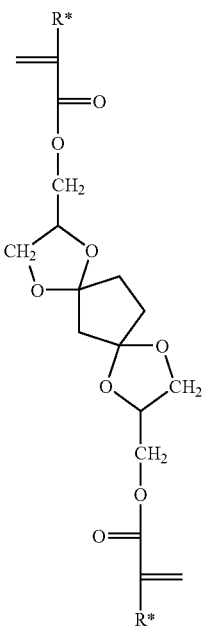

In Formula 7a, R* is hydrogen or methyl.

EXAMPLE 1-2

Preparation of Monomer of Formula 7b

Except for adding 11.2 g of cyclohexane-1,4-dione instead of 9.8 g of cyclopentane-1,3-dione, the monomer represented by the following Formula 7b was obtained with 50% yield in the same manner as described in Example 1-1. {H-NMR: i)R*=H, d(6.46, 2H), m(6.16, 2H), d(5.88, 2H), m(4.36, 2H), m(4.21, 4H), m(4.11, 2H), m(3.79, 2H), m(1.85, 8H) ii) R*=CH$_3$, s(6.16, 2H), d(5.88, 2H), m(4.36, 2H), m(4.21, 4H), m(4.11, 2H), m(3.79, 2H), m(1.85, 14H)}

[Formula 7b]

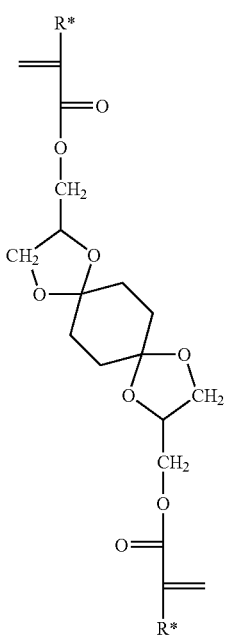

In Formula 7b, R* is hydrogen or methyl.

EXAMPLE 1-3

Preparation of Monomer of Formula 7c

Except for adding 16.6 g of 1,5-dimethylbicyclo[3,3,0]octane-3,7-dione instead of 9.8 g of cyclopentane-1,3-dione, the monomer represented by the following Formula 7c was obtained with 55% yield in the same manner as described in Example 1-1. {H-NMR: i)R*=H, d(6.46, 2H), m(6.13, 2H), d(5.38, 2H), m(4.89, 2H), m(4.71, 4H), m(4.31, 2H), m(3.52, 2H), m(1.85, 16H) ii) R*=CH$_3$, s(6.36, 2H), d(5.68, 2H), m(4.86, 2H), m(4.36, 4H), m(4.14, 2H), m(3.69, 2H), m(1.25, 22H)}

[Formula 7c]

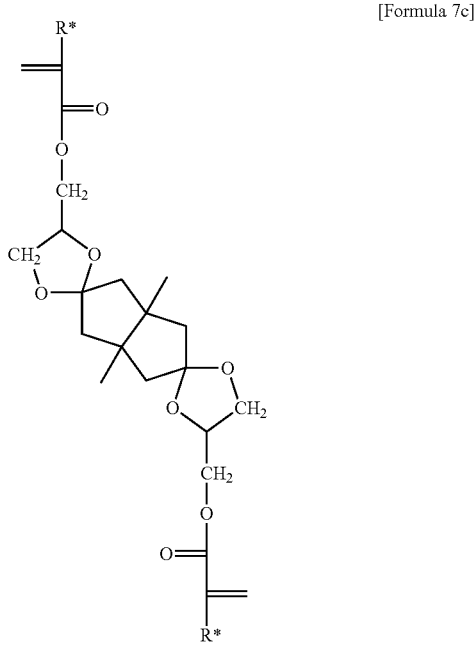

In Formula 7c, R* is hydrogen or methyl.

EXAMPLE 1-4

Preparation of Monomer of Formula 7d

Except for adding 15.2 g of 7,7-dimethyl norbornane-2,3-dione instead of 9.8 g of cyclopentane-1,3-dione, the monomer represented by the following Formula 7d was obtained with 65% yield in the same manner as described in Example 1-1. {H-NMR: i)R*=H, d(6.05, 2H), m(6.25, 2H), d(5.18, 2H), m(4.86, 2H), m(4.61, 4H), m(4.31, 2H), m(3.29, 2H), m(1.25, 12H) ii) R*=CH$_3$, s(6.16, 2H), d(5.86, 2H), m(4.86, 2H), m(4.51, 4H), m(4.21, 2H), m(3.29, 2H), m(1.75,18H)}

[Formula 7d]

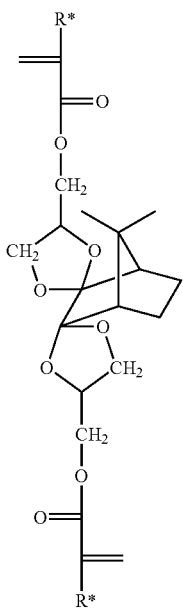

In Formula 7d, R* is hydrogen or methyl.

EXAMPLE 1-5

Preparation of Monomer of Formula 7e

Except for adding 16.4 g of adamantane-2,6-dione instead of 9.8 g of cyclopentane-1,3-dione, the monomer represented by the following Formula 7e was obtained with 55% yield in the same manner as described in Example 1-1. {H-NMR: i)R*=H, d(6.86, 2H), m(6.15, 2H), d(5.52, 2H), m(4.95, 2H), m(4.61, 4H), m(4.55, 2H), m(3.52, 2H), m(1.25, 12H) ii) R*=CH$_3$, s(6.56, 2H), d(5.68, 2H), m(4.66, 2H), m(4.45, 4H), m(4.15, 2H), m(3.45, 2H), m(1.85, 18H)}

[Formula 7e]

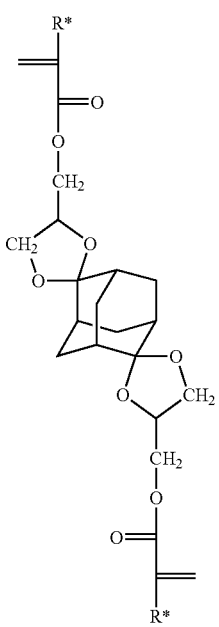

In Formula 7e, R* is hydrogen or methyl.

EXAMPLE 1-6

Preparation of Monomer of Formula 7f

Except for adding 23.6 g of 2,2-bis-4'-oxo cyclohexyl propane instead of 9.8 g of cyclopentane-1,3-dione, the monomer represented by the following Formula 7f was obtained with 50% yield in the same manner as described in Example 1-1. {H-NMR: i)R*=H, d(6.20, 2H), m(6.01, 2H), d(5.80, 2H), m(4.96, 2H), m(4.38, 4H), m(4.21, 2H), m(3.29, 2H), m(1.35, 24H) ii) R*=CH$_3$, s(6.36, 2H), d(5.88, 2H), m(4.66, 2H), m(4.21, 4H), m(4.01, 2H), m(3.79, 4H), m(1.55, 30H)}

[Formula 7f]

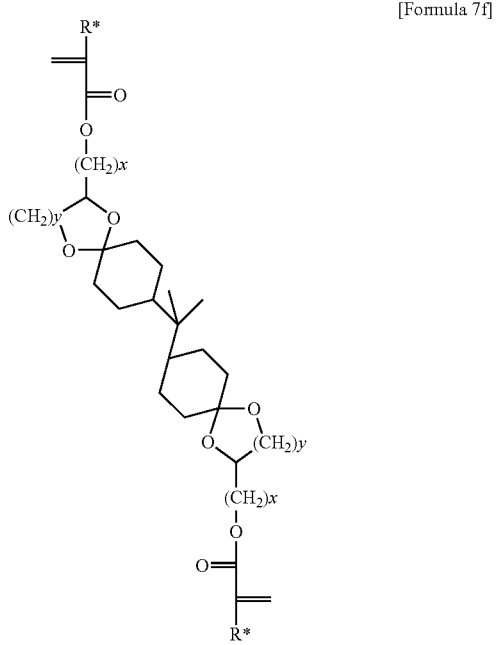

In Formula 7f, R* is hydrogen or methyl.

EXAMPLE 1-7

Preparation of Monomer of Formula 7q

Except for adding 31.2 g of normal pentane-1,3,5-triol instead of 24.0 g of glycerol, the monomer represented by the following Formula 7 g was obtained with 50% yield in the same manner as described in Example 1-5. {H-NMR: i)R*=H, d(6.43, 2H), m(6.05, 2H), d(5.80, 2H), m(4.15, 4H), m(3.80, 6H), m(1.35, 20H) ii) R*=CH$_3$, s(6.15, 2H), d(5.58, 2H), m(4.15, 4H), m(3.80, 6H), m(2.02, 26H)}

[Formula 7g]

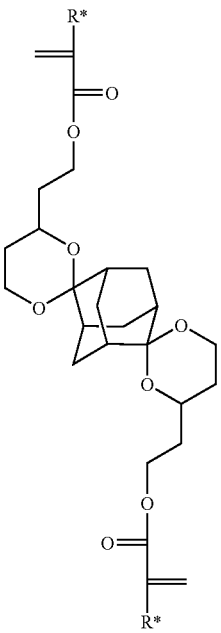

In Formula 7 g, R* is hydrogen or methyl.

EXAMPLE 2-1

Preparation of Polymer of Formula 3a 35.8 g (0.1 mol) of the monomer represented by Formula 7a (R*=methyl), 22.2 g (0.1 mol) of 2-methyl-2-adamantyl methacrylate and 0.7 g of azobisisobutyronitrile (AIBN) were added into a reactor, and the reactant was dissolved in 25 g of tetrahydrofuran (THF). Subsequently, the gas in the reactor was removed by a freezing method with a ampoule, and the polymerization reaction was carried out at 68° C. for 24 hours. After completion of the polymerization reaction, the reactant was slowly dropped to a lot of diethylether and was precipitated in diethylether. Then, the precipitant was dissolved in tetrahydrofuran (THF) again, and the dissolved reactant was re-precipitated in diethylether to obtain the polymer (R* and R**=methyl, x=1, y=1) represented by Formula 3a (Mw (=weight average molecular weight): 15,200, PD (=polydispersity): 2.32).

EXAMPLE 2-2

Preparation of Polymer of Formula 3b

Except for adding 37.2 g (0.1 mol) of the monomer (R*=methyl) represented by Formula 7b instead of 35.8 g (0.1 mol) of the monomer (R*=methyl) represented by Formula 7a, the polymer (R* and R**=methyl, x=1, y=1) represented by above-mentioned Formula 3b was obtained in the same manner as described in Example 2-1 (Mw: 12,500, PD: 2.12).

EXAMPLE 2-3

Preparation of Polymer of Formula 3c

Except for adding 42.8 g (0.1 mol) of the monomer (R*=methyl) represented by Formula 7c instead of 35.8 g (0.1 mol) of the monomer (R*=methyl) represented by Formula 7a, the polymer (R* and R**=methyl, x=1, y=1) represented by above-mentioned Formula 3c was obtained in the same manner as described in Example 2-1 (Mw: 9,200, PD: 1.89).

EXAMPLE 2-4

Preparation of Polymer of Formula 3d

Except for adding 41.2 g (0.1 mol) of the monomer (R*=methyl) represented by Formula 7d instead of 35.8 g (0.1 mol) of the monomer (R*=methyl) represented by Formula 7a, the polymer (R* and R**=methyl, x=1, y=1) represented by above-mentioned Formula 3d was obtained in the same manner as described in Example 2-1 (Mw: 10,900, PD: 1.96).

EXAMPLE 2-5

Preparation of Polymer of Formula 3e

Except for adding 42.4 g (0.1 mol) of the monomer (R*=methyl) represented by Formula 7e instead of 35.8 g (0.1 mol) of the monomer (R*=methyl) represented by Formula 7a, the polymer (R* and R**=methyl, x=1, y=1) represented by above-mentioned Formula 3e was obtained in the same manner as described in Example 2-1 (Mw: 9,200, PD: 2.12).

EXAMPLE 3-1

Preparation of Polymer of Formula 5a 35.8 g (0.1 mol) of the monomer represented by Formula 7a (R*=methyl), 14.3 g (0.05 mol) of 2-methyl-2-adamantyl-5-norbornyl-2-carboxylate, 4.9 g (0.05 mol) of maleic anhydride, 22.2 g (0.1 mol) of 2-methyl-2-adamantyl methacrylate and 0.7 g of azobisisobutyronitrile (AIBN) were added into a reactor, and the reactant was dissolved in 45 g of tetrahydrofuran (THF). Subsequently, the gas in the reactor was removed by a freezing method with a ampoule, and the polymerization reaction was carried out at 68□ for 24 hours. After completion of the polymerization reaction, the reactant was slowly dropped to a lot of diethylether and was precipitated in diethylether. Then, the precipitant was dissolved in tetrahydrofuran (THF) again, and the dissolved reactant was re-precipitated in diethylether to obtain the polymer (R*=methyl, x=1, y=1) represented by above mentioned Formula 5a (Mw: 14,200, PD: 2.02).

EXAMPLE 3-2

Preparation of Polymer of Formula 5b

Except for adding 37.2 g (0.1 mol) of the monomer (R*=methyl) represented by Formula 7b instead of 35.8 g (0.1 mol) of the monomer (R*=methyl) represented by Formula 7a, the polymer (R*=methyl, x=1, y=1) represented by above-mentioned Formula 5b was obtained in the same manner as described in Example 3-1 (Mw: 9,500, PD: 1.95).

EXAMPLE 3-3

Preparation of Polymer of Formula 5c

Except for adding 42.8 g (0.1 mol) of the monomer (R*=methyl) represented by Formula 7c instead of 35.8 g (0.1 mol) of the monomer (R*=methyl) represented by Formula 7a, the polymer (R*=methyl, x=1, y=1) represented by above-mentioned Formula 5c was obtained in the same manner as described in Example 3-1 (Mw: 9,800, PD: 1.96).

EXAMPLE 3-4

Preparation of Polymer of Formula 5d

Except for adding 41.2 g (0.1 mol) of the monomer (R*=methyl) represented by Formula 7d instead of 35.8 g (0.1 mol) of the monomer (R*=methyl) represented by Formula 7a, the polymer (R*=methyl, x=1, y=1) represented by above-mentioned Formula 5d was obtained in the same manner as described in Example 3-1 (Mw: 13,500, PD: 1.93)

EXAMPLE 3-5

Preparation of Polymer of Formula 5e

Except for adding 42.4 g (0.1 mol) of the monomer (R*=methyl) represented by Formula 7e instead of 35.8 g (0.1 mol) of the monomer (R*=methyl) represented by Formula 7a, the polymer (R* and R**=methyl, x=1, y=1) represented by above-mentioned Formula 5e was obtained in the same manner as described in Example 3-1 (Mw: 11,200, PD: 2.16).

EXAMPLE 3-6

Preparation of Polymer of Formula 5f

Except for adding 46.7 g (0.1 mol) of the monomer (R*=methyl) represented by Formula 7f instead of 35.8 g (0.1 mol) of the monomer (R*=methyl) represented by Formula 7a, the polymer (R* and R**=methyl, x=1, y=1) represented by above-mentioned Formula 5f was obtained in the same manner as described in Example 3-1 (Mw: 8,600, PD: 1.91).

EXAMPLES 4-1 to 4-11

Preparation of Photoresist Composition Including Polymer Obtained from Examples 2-1 to 2-5 and Examples 3-1 to 3-6

2 g of polymer, which was obtained in Example 2-1, 0.024 of phthalimido trifluoromethane sulfonate and 0.06 g of triphenylsulfonium triflate were dissolved in 20 g of propyleneglycolmonomethyl etheracetate (PGMEA), and then a photoresist composition was prepared by filtering with a filter of 0.20 μm pore size (Example 4-1). Besides, Except for adding 2 g of polymer, which was prepared in Examples 2-2 to 2-5 and 3-1 to 3-6 instead of 2 g of polymer, which was prepared in Example 2-1, photoresist compositions were prepared in the same manner as described in Example 4-1 (Examples 4-2 to 4-11).

EXAMPLE 5-1 to 5-11

Formation of Photoresist Pattern

Figure 2:
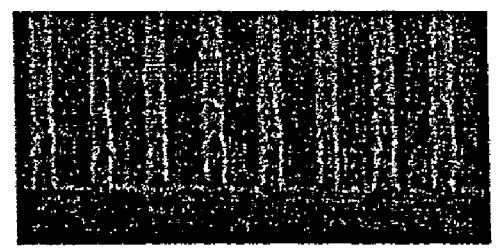
Figure 3:
Figure 4:
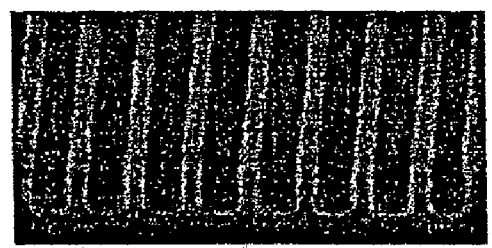
Figure 5:
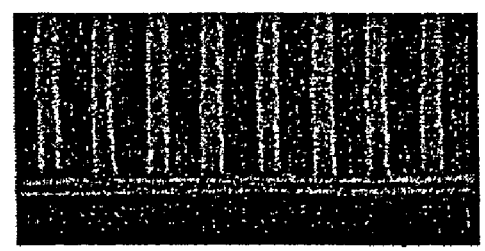
Figure 6:
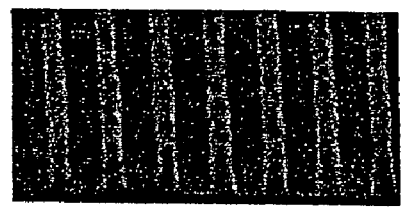
Figure 7:
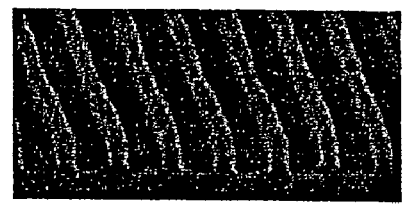
Figure 8:
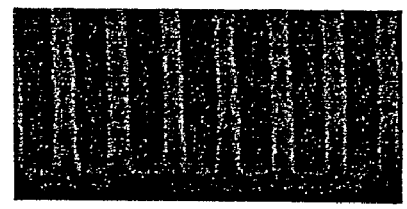
Figure 9:
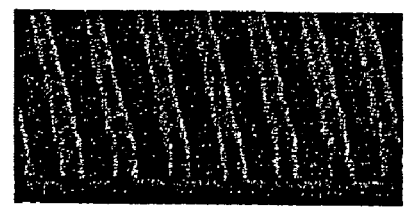
Figure 10:
Figure 11:
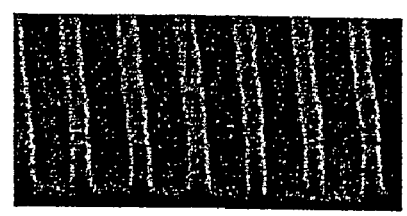

The photoresist compositions prepared in Examples 4-1 to 4-11 were spin coated on the upper parts of silicon wafers to prepare thin-films of photoresist. The photoresist layer was pre-baked at a temperature of 90° C. for 90 seconds in a oven or on a hot plate, and was exposed with an ArF excimer laser, and was post-baked at a temperature of 120° C. for 90 seconds. Thereafter, the baked wafer was developed with 2.38 weight % of TMAH solution for about 40 seconds, thereby forming a 0.07 μm line/space patterns. The properties of the produced photoresist patterns were shown in Table 1, SEM (Scanning Electron Microscopy) pictures of the photoresist patterns which were formed with the photoresist compositions of Examples 4-1 to 4-11 were shown in FIGS. 1 to 11.

TABLE 1

| Resist composition | Minimum resolution [μm] | focus depth [μm] | Line Edge Roughness [nm] | energy process margin [%] | post exposure bake sensitivity [nm/° C.] | dry etching resistance |
|---|---|---|---|---|---|---|
| Example 5-1  | 0.065 | 0.30 | 5.5 | 12.0 | 6   | good |
| Example 5-2  | 0.065 | 0.30 | 5.5 | 12.5 | 4   | good |
| Example 5-3  | 0.065 | 0.35 | 4.7 | 15.0 | 1   | good |
| Example 5-4  | 0.065 | 0.45 | 4.5 | 13.0 | 2   | very good |
| Example 5-5  | 0.065 | 0.45 | 4.5 | 13.5 | 1   | very good |
| Example 5-6  | 0.065 | 0.35 | 6.0 | 12.5 | 3   | good |
| Example 5-7  | 0.065 | 0.35 | 5.6 | 13.2 | 2   | very good |
| Example 5-8  | 0.065 | 0.40 | 5.0 | 15.5 | 1   | good |
| Example 5-9  | 0.065 | 0.45 | 5.6 | 13.3 | 1.5 | very good |
| Example 5-10 | 0.065 | 0.45 | 5.3 | 13.5 | 1   | very good |
| Example 5-11 | 0.065 | 0.45 | 4.8 | 11.0 | 1   | very good |

The photoresist monomer having a spiro cyclic ketal group, the polymer thereof and the photoresist composition including the same according to the present invention can improve the resolution and the process margin, because activation energy of the deprotection reaction of the spiro cyclic ketal group is low, and also can produce fine photoresist patterns because they have a high dry etching resistance and stable PEB :(Post Exposure Baking) temperature sensitivity. Further, the photoresist polymers and photoresist compositions including the same can improve the focus depth margin and the line edge roughness of the resist layer.

What is claimed is:

1. A monomer of the following Formula 1,

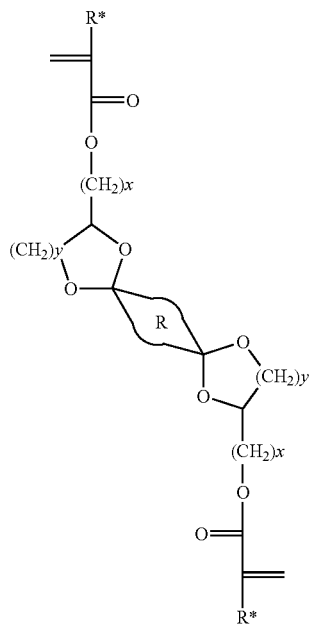

[Formula 1]

in Formula 1, R* is hydrogen or methyl group, x and y are independently 1, 2 or 3, and R is a mono-cyclic or multi-cyclic homo or hetero saturated hydrocarbyl group of 3 to 50 carbon atoms.

2. The monomer according to claim 1, wherein R is selected from the group consisting of

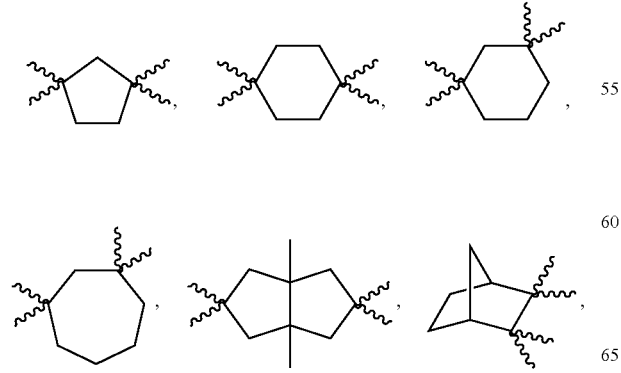

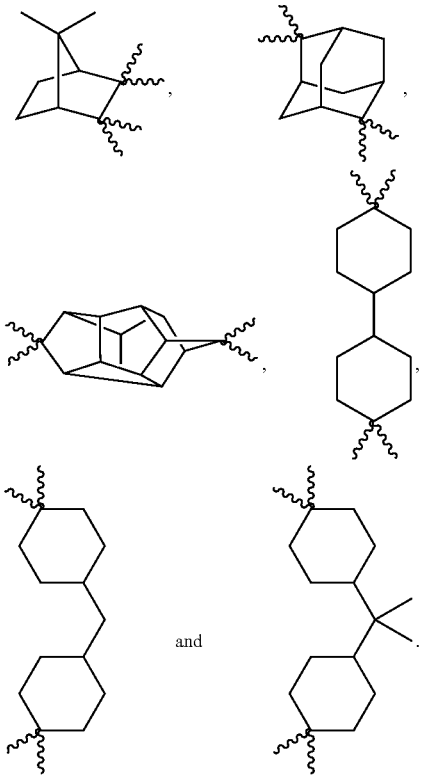

3. The monomer according to claim 1, wherein the monomer is prepared by the reaction of cyclic ketone and trialcohol under an acid catalyst.

4. A photoresist polymer including a repeating unit of the following Formula 2,

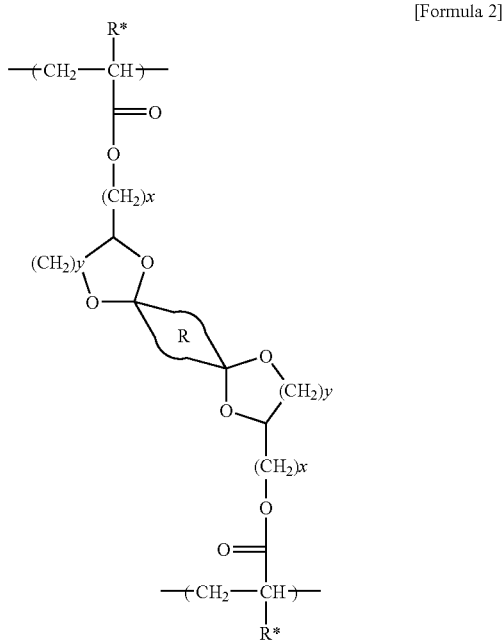

[Formula 2]

in Formula 2, R*, R, x and y are as defined in Formula 1.

5. The photoresist polymer according to claim 4, wherein the photoresist polymer is represented by the following Formula 3,

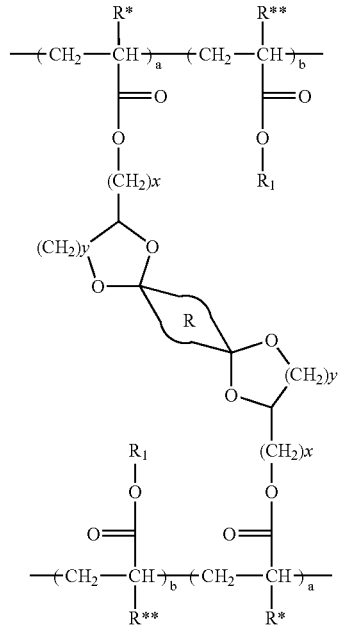

[Formula 3]

in Formula 3, R* and R** are independently hydrogen or a methyl group, $R_1$ can be the same or different, and is a chain type or ring type alkyl group of 1 to 20 carbon atoms, a and b are mole % of the repeating units composing the upper and lower polymer chains, and are independently 1~99 mol % and 1~99 mol %, and x, y, and R are as defined in Formula 1.

6. The photoresist polymer according to claim 4, wherein the photoresist polymer is selected from the group consisting of polymers of the following Formulas 3a to 3e,

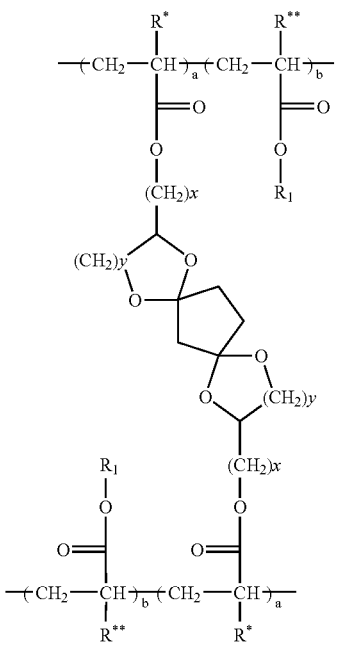

[Formula 3a]

-continued

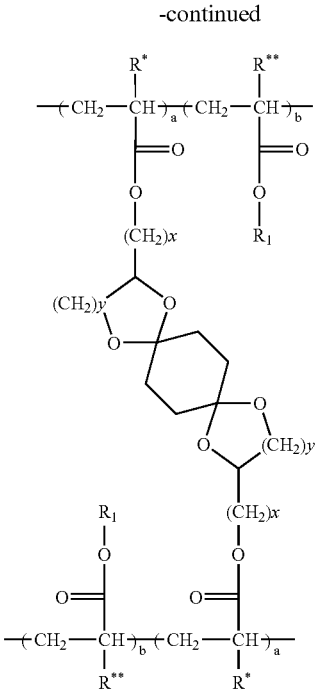

[Formula 3b]

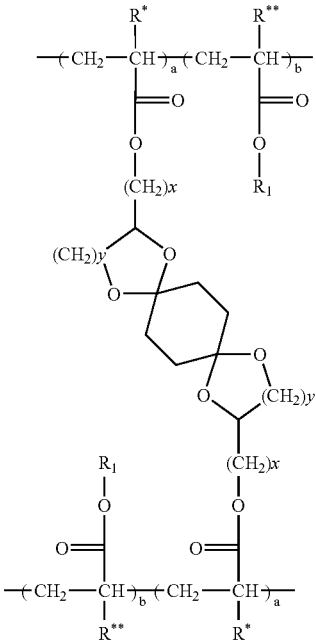

[Formula 3c]

[Formula 3d]

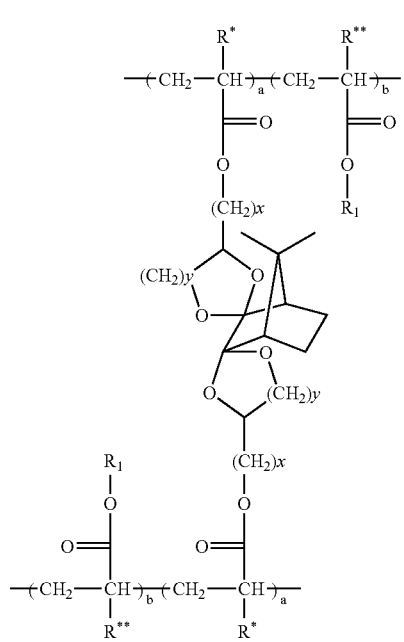

[Formula 3e]

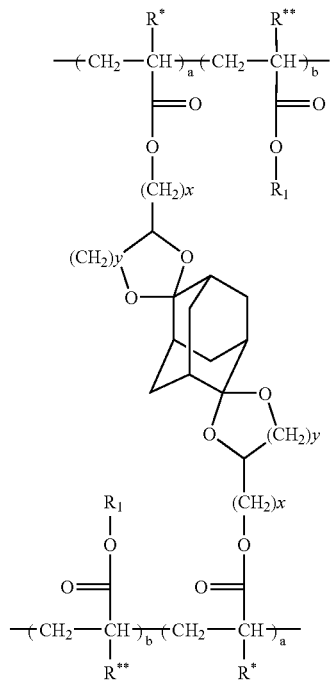

[Formula 4]

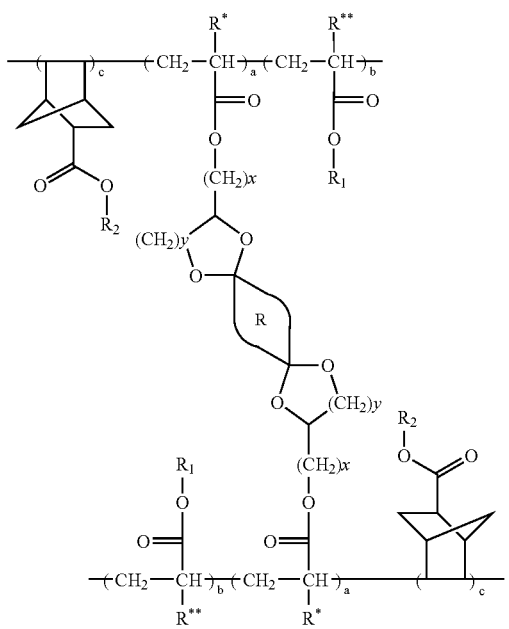

[Formula 5]

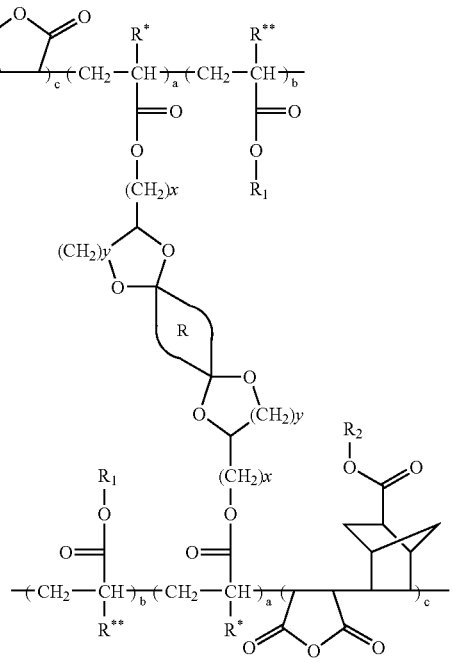

in Formulas 3a to 3e, R*, R**, R, $R_1$, a, b, x and y are as defined in Formula 3.

7. The photoresist polymer according to claim 4, wherein the photoresist polymer is represented by the following Formulas 4 or 5, in Formulas 4 and 5, R* and R** are independently hydrogen or a methyl group, $R_1$ can be the same or different, and is a chain type or ring type alkyl group of 1 to 20 carbon atoms, R is a mono-cyclic or multi-cyclic homo or hetero saturated hydrocarbyl group of 3 to 50 carbon atoms, x and y are independently 1, 2, or 3, and a, b and c are mole % of the repeating units composing the upper and lower polymer chains, and are independently 1~95 mol %, 1~95 mol %, and 1~95 mol %.

8. The photoresist polymer according to claim 4, wherein the photoresist polymer is selected from the group consisting of polymers of the following Formulas 5a to 5f,

[Formula 5a]

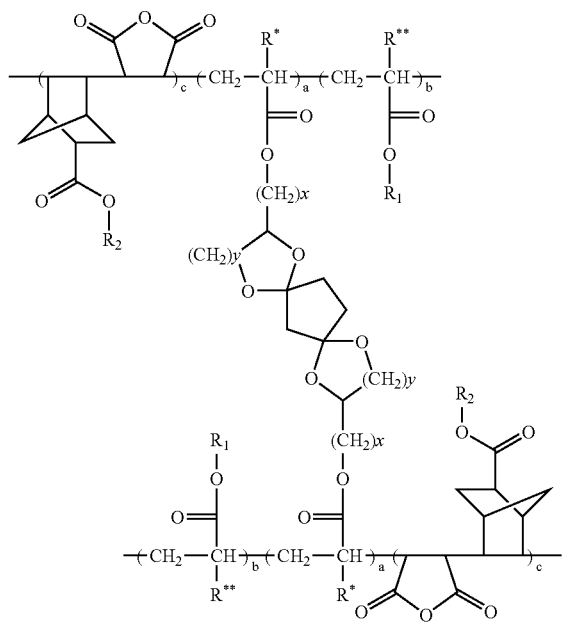

[Formula 5b]

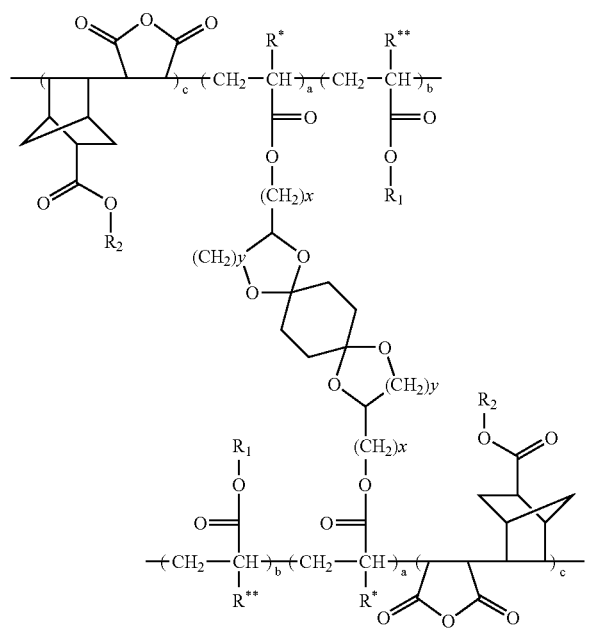

-continued

[Formula 5c]

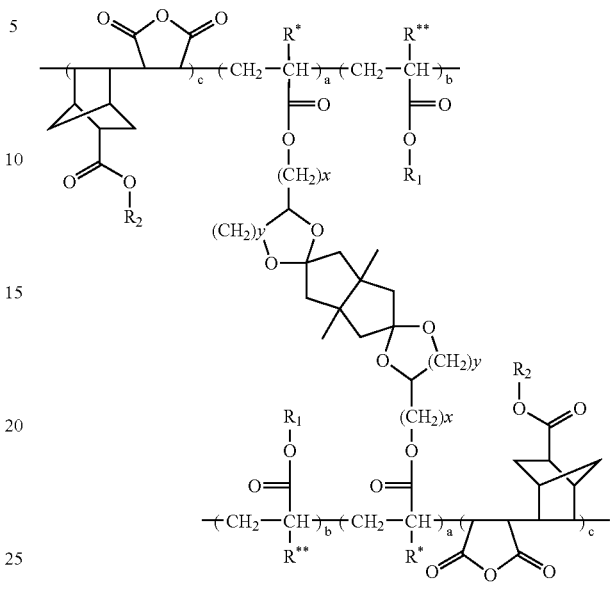

[Formula 5d]

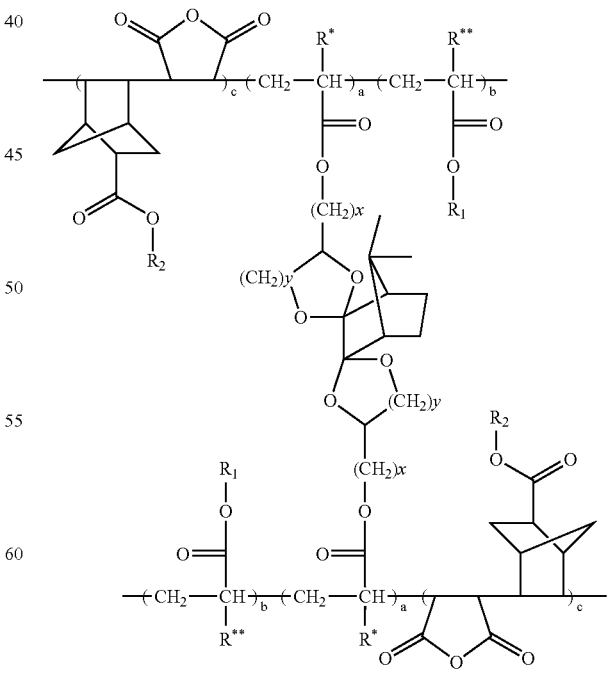

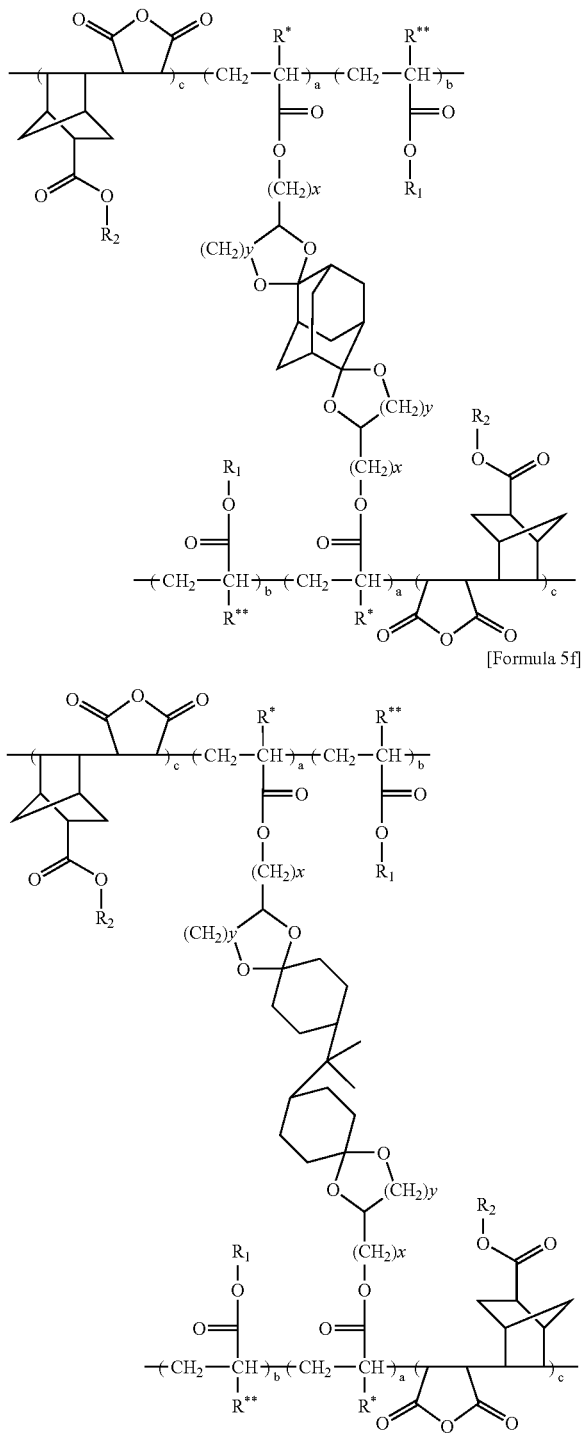

[Formula 5e]

[Formula 5f]

in Formulas 5a to 5f, R*, R**, R, $R_1$, $R_2$, a, b, c, x and y are as defined in Formula 4 and 5.

9. A photoresist composition comprising:
a photoresist polymer of claim 4;
a photo-acid generator for producing an acid component; and
an organic solvent.

10. The photoresist composition according to claim 9, wherein the amount of the photosensitive polymer 1 to 30 weight % for the total amount of the photoresist composition, and the amount of the photo-acid generator is from 0.05 to 10 weight % for the amount of the photoresist polymer.

11. The photoresist composition according to claim 9, wherein the photo-acid generator is selected from the group consisting of phthalimidotrifluoromethane sulfonate, dinitrobenzyltosylate, n-decyl disulfone, naphthylimido trifluoromethane sulfonate, diphenyliodonium hexafluorophosphate, diphenyliodonium hexafluoroarsenate, diphenyliodonium hexafluoroantimonate, diphenylparamethoxyphenylsulfonium triflate, diphenylparatoluenylsulfonium triflate, diphenylpara-isobutyl phenylsulfonium triflate, triphenylsulfonium hexafluoroarsenate, triphenylsulfonium hexafluoro antimonate, triphenylsulfonium triflate, dibutyinaphthylsulfonium triflate and the mixtures thereof.

12. The photoresist composition according to claim 9, wherein the organic solvent is selected from the group consisting of ethyleneglycol monomethylether, ethyleneglycol monoethylether, ethyleneglycol monoacetate, diethyleneglycol, diethyleneglycol monoethylether, propyleneglycol monomethyletheracetate, propyleneglycol, propyleneglycol monoacetate, toluene, xylene, methylethylketone, methylisoamylketone, cyclohexanone, dioxane, methyl lactate, ethyl lactate, methylpyruvate, ethyl pyruvate, methylmethoxy propionate, ethylmethoxy propionate, N,N-dimethyl formamide, N,N-dimethyl acetamide, N-methyl 2-pyrrolidone, 3-ethoxyethylpropionate, 2-heptanone, gamma-butyrolactone, ethyl 2-hydroxy propionate, ethyl 2-hydroxy-2-methyl propionate, ethoxyethyl acetate, hydroxyethyl acetate, methyl 2-hydroxy-3-methylbutanoate, methyl 3-methoxy-2-methylpropionate, ethyl 3-ethoxy propionate, ethyl 3-methoxy-2-methylpropionate, ethyl acetate, butyl acetate and the mixtures thereof.

13. A method of forming a photoresist pattern comprising the steps of:
forming a photoresist layer by applying the photoresist composition including a photoresist polymer of claim 4, a photo-acid generator for producing an acid component, and an organic solvent on a substrate; and
forming a predetermined photoresist pattern by exposing the photoresist layer to a light source; and
developing the photoresist pattern.

* * * * *